Dec. 8, 1959 R. L. BYRUM Plant Pat. 1,886
ROSE PLANT
Filed March 13, 1959
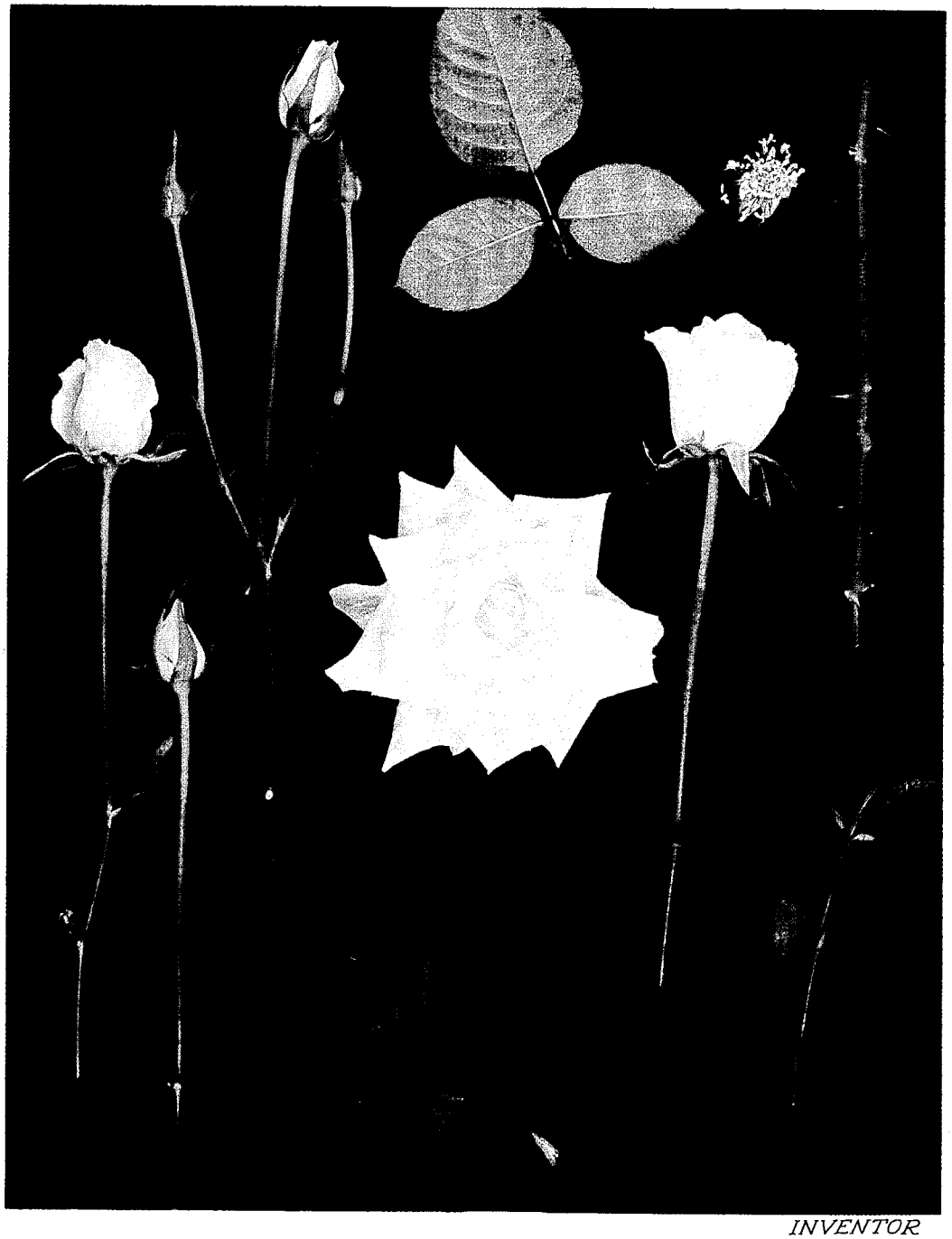
INVENTOR
R. L. Byrum
BY Robb & Robb
ATTORNEYS United States Patent Office Plant Pat. 1,886
Patented Dec. 8, 1959

1,886

ROSE PLANT

Roy L. Byrum, Richmond, Ind., assignor to Joseph H. Hill Company, Richmond, Ind., a corporation of Indiana Application March 13, 1959, Serial No. 799,393

1 Claim. (Cl. 47—61)

The present invention relates to a new and distinct variety of rose plant of the large-flowered polyantha class, which was originated by me by crossing an unnamed and unpatented seedling identified in my breeding records as No. 52/40W, with the variety "White Butterfly" (Plant Patent No. 1,337).

The primary objective of this breeding was to produce an improved white rose having both the good qualities of the variety "White Butterfly," and flowers of greater petalage which are borne with a longer "stretch" on the stems. This objective was at least partially achieved, along with other improvements, as evidenced by the fact that the resulting new variety is of the floribunda type and is characterized by the following features which are outstanding therein and which represent a unique combination which distinguishes it from its parents, as well as from all other varieties of which I am aware:

(1) Good bloom production suitable for the commercial production of cut flowers and better than the cut flower production of both the parent variety "White Butterfly" and that of the variety "White Bouquet" (Plant Patent No. 1,415) which the present variety somewhat resembles;

(2) A slow-opening flower habit, with consequent long-lasting flower qualities superior to those of the variety "White Bouquet";

(3) Greater flower petalage than that of the variety "White Butterfly"; and (4) A distinctive white general color tonality of the blooms.

Asexual reproduction of my new variety by both grafting and budding, as performed at Richmond, Indiana, and also by budding, as performed at West Grove, Pennsylvania, shows that the aforementioned characteristics and distinctions come true to form and are established and transmitted through succeeding propagations.

The accompanying drawing shows typical specimens of the vegetative growth and flowers of my new variety, in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson"), Ridgway's Color Standards and Nomenclature (hereinafter abbreviated as "Ridgway"), and Koster's Color Guide (hereinafter abbreviated as "Koster"), except where general color terms of ordinary dictionary significance are obvious:

Type: Greenhouse; bush; seedling.
Class:
*Botanic.*—Large-flowered polyantha.
*Commercial.*—Floribunda.
Breeding: Seedling.
*Seed parent.*—An unnamed seedling identified in my breeding records as No. 52/40W.
*Pollen parent.*—"White Butterfly."

Propagation: Holds its distinguishing characteristics through succeeding propagations by both grafting and budding.

*Flower*

Locality where grown and observed: Richmond, Indiana.
Flowers borne: Both singly and in clusters, but can be grown on single stems for commercial production of cut flowers; on stems of medium strength and medium length.
Quantity of bloom: Abundant, in greenhouse.
Continuity: Continuous.
Fragrance: Slight. Nature—tea.
Bud:
*Peduncle.*—Short; medium diameter; erect. Bark—smooth; color—Scheeles Green, Plate 860/2 (Wilson). Thorns — none. Prickles — none. Hairs—few; color—Pure White, Plate 1 (Koster).
*Before calyx breaks.*—Size—small. Form—short pointed; with a conspicuous neck; with foliaceous appendages on the surface of the bud; with slender, foliaceous parts extending beyond the tip of the bud equal to ¾ or more of its length. Color—Scheeles Green, Plate 860/1 (Wilson).
*As calyx breaks.*—Color (outside of petal)—Sap Green, Plate 62/3 (Wilson).
*As first petal opens.*—Size—medium small. Form—pointed; ovoid. Color: outside—white, with very light streaks or veins of Sap Green, Plate 62/3 (Wilson); inside—white, with light streaks or veins of from Sap Green, Plate 62/3 (Wilson) to Sap Green, Plate 62/2 (Wilson).
*Opening.*—Opens up well in greenhouse; no unusual characteristics attributed to weather conditions.
Bloom:
*Size (when fully open).*—Medium small; from 2 inches to 3 inches; when grown for cut flower production with single bloom per stem, size is about same as that of "Garnette" (unpatented) and "Carol Amling" (Plant Patent No. 1,126).
*Petalage.*—Very double (many petals, usually with no stamens showing); from 45 to 50 petals; arranged irregularly.
*Form.*—Flat and full at first, but becoming open; petals being at first tightly rolled outward, but later becoming loosely rolled outward at maturity.
Petals:
*Texture.*—Moderately thick. Inside—satiny. Outside—satiny.
*Shape.*—Outer petals—obovate, with apex obtuse. Intermediate petals—obovate, with apex obtuse. Inner petals—obovate, with apex obtuse.

This description of a newly opened flower was made from a rose grown in a greenhouse in the month of June, at Richmond, Indiana:

*Color.*—Outer petals: outside surface—white, with very light veins or streaks of Sap Green, Plate 62/3 (Wilson); inside surface—white, with very light veins or streaks of Sap Green, Plate 62/3 (Wilson). Intermediate petals: outside surface—white, with base of petal Chartreuse Green, Plate 663/3 (Wilson); inside surface—white, with base of petal Chartreuse Green, Plate 663/3 (Wilson). Inner petals: outside surface—white at top of petal, gradually changing to Chartreuse Green, Plate 663/3 (Wilson) at base of petal; inside surface—white at top of petal, gradually changing to Chartreuse Green, Plate 663/3 (Wilson) at base of petal.

This description was made from a rose that was open for 3 days in a greenhouse in the month of June at Richmond, Indiana:

*Color.*—Outer petals: outside surface—white, with very light streaks or veins of Sap Green, Plate 62/3 (Wilson); inside surface—white, with very light streaks or veins of Sap Green, Plate 62/3 (Wilson). Intermediate petals: outside surface—white, with base of petal Chartreuse Green, Plate 663/3 (Wilson); inside surface—white, with base of petal Chartreuse Green, Plate 663/3 (Wilson). Inner petals: outside surface—white at top of petal, gradually changing to Chartreuse Green, Plate 663/3 (Wilson) at base of petal; inside surface—white at top of petal, gradually changing to Chartreuse Green, Plate 663/3 (Wilson) at base of petal.

*General color effect.*—Newly opened flower—white. 3-days open—white.

*Behavior.*—Persist in greenhouse; fading to white.

*Flower longevity.*—Cut roses grown in greenhouse and kept at living-room temperatures—5 or 6 days in November.

*Reproductive organs*

Stamens: Medium number; arranged regularly about pistils; mixed with petaloids.

Filaments: Short; most with anthers. Color—Rose Bengal, Plate 25/1 (Wilson).

Anthers: Small; all open at once. Color—Mimosa Yellow, Plate 602/3 (Wilson).

Pollen: Moderate abundance. Color—Chinese Yellow, Plate 606/2 (Wilson).

Pistils: Many.

Styles: Uneven; medium length; thin; bunched. Color—Pure White, Plate 1 (Koster).

Stigma: Color—Pure White, Plate 1 (Koster).

Ovularies: Some protruding from calyx.

Hips: None.

Sepals: Permanent; medium length; straight. Color: inside—Spinach Green, Plate 0960/1 (Wilson), with streak of Pod Green, Plate 061/2 (Wilson), through center, and overlaid with white fuzz; outside—Spinach Green, Plate 0960/1 (Wilson).

Seeds: None.

*Plant*

Foliage:

*Leaves.*—Compound of 5 leaflets; abundant; medium size; heavy; leathery.

*Leaflets.* — Shape — elliptical. Apex — acuminate. Base—round. Margin—simply serrate.

*Color.*—Mature: upper surface — near Spinach Green, Plate 0960 (Wilson), with margin Violet, Plate 59 (Koster); under surface—near Apple Green, Plate 77 (Koster), with some overlaid with shades of Violet, Plate 59 (Koster). Young: upper surface—Pea Green, Plate 61/2 (Wilson), overlaid with Vandyke Red, Plate XIII (Ridgway); under surface—Pea Green, Plate 61/2 (Wilson), overlaid with Acajou Red, Plate XIII (Ridgway).

*Rachis (the supporting stem of the compound leaf).*—Medium light. Upper side—smooth; grooved. Under side—sparsely prickly.

*Stipules.*—Moderately short; narrow; with very short points turning out at an angle of less than 45°.

Growth:

*Habit.*—Bush; upright; much-branched.

*Growth.*—Free; vigorous.

*Canes.*—Medium diameter.

*Main stems.*—Color—Spinach Green, Plate 0960/3 (Wilson), overlaid or streaked with Van Dyck Brown, Plate 96 (Koster). Thorns—several; medium length; some straight and some hooked downward; with short, narrow base; color—Van Dyck Brown, Plate 96 (Koster). Prickles—none. Hairs—none.

*Branches.*—Color—Spinach Green, Plate 0960/2 (Wilson). Thorns—several; short; hooked downward; with short, narrow base; color—Violet Rose, Plate 39 (Koster). Prickles — none. Hairs — none.

*New shoots.*—Color—near Vandyke Red, Plate XIII (Ridgway). Thorns—several; medium length; hooked downward; with very short, narrow base; color—from Rose Opal, Plate 022/2 (Wilson) to Rose Opal, Plate 022/1 (Wilson). Prickles—none. Hairs—none.

I claim:

A new and distinct variety of rose plant of the large-flowered polyantha class, substantially as herein shown and described, characterized particularly as to novelty by the unique combination of good bloom production and consequent suitability for commercial production of cut flowers borne on single stems, a relatively slow-opening habit of the flowers, good petalage, long-lasting quality of the blooms, and a distinctive white general color tonality of the blooms.

No references cited.

Dedication

Plant Pat. No. 1,886.—*Roy L. Byrum*, Richmond, Ind. ROSE PLANT. Patent dated Dec. 8, 1959. Dedication filed Sept. 21, 1971, by the assignee, *Joseph H. Hill Company*.

Hereby dedicates its entire interest in the said patent to the Public of the United States.

[*Official Gazette November 9, 1971.*]